United States Patent [19]

Mantegani et al.

[11] Patent Number: 5,210,194
[45] Date of Patent: May 11, 1993

[54] PROCESS FOR PREPARING ERGOLINE DERIVATIVES

[75] Inventors: Sergio Mantegani; Gabriella Traquandi, both of Milan; Tiziano Bandiera, Gambolo; Enzo Brambilla, Mariano Comense, all of Italy

[73] Assignee: Farmitalia Carlo Erba S.r.l. An Italian Body Corporate, Milan, Italy

[21] Appl. No.: 761,977

[22] PCT Filed: Jan. 21, 1991

[86] PCT No.: PCT/EP91/00104

§ 371 Date: Sep. 25, 1991

§ 102(e) Date: Sep. 25, 1991

[87] PCT Pub. No.: WO91/11447

PCT Pub. Date: Aug. 8, 1991

[30] Foreign Application Priority Data

Jan. 25, 1990 [GB] United Kingdom ............... 9001774
Nov. 28, 1990 [GB] United Kingdom ............... 9025849

[51] Int. Cl.[5] ............................................ C07D 457/02
[52] U.S. Cl. ................................. 544/361; 544/385
[58] Field of Search .............................. 544/361, 385

[56] References Cited

U.S. PATENT DOCUMENTS

| | | | |
|---|---|---|---|
| 3,763,161 | 10/1973 | Hartter | 544/408 |
| 4,690,929 | 9/1987 | Bernardi et al. | 544/361 |
| 4,728,649 | 3/1988 | Mantegani et al. | 544/361 |
| 4,806,538 | 2/1989 | Shimazaki et al. | 544/364 |
| 4,871,736 | 10/1989 | Nair et al. | 544/408 |
| 4,940,709 | 7/1990 | Shimazaki et al. | 544/364 |

FOREIGN PATENT DOCUMENTS 126968 12/1984 European Pat. Off.
197241 10/1986 European Pat. Off.

OTHER PUBLICATIONS

J. W. Dubsky et al, Chem. Ber. vol. 52, 1919 "Zur Kenntnis der Diketopiperazine" pp. 221-234.

B. P. Das et al, Chem. Abst. vol. 70, No. 9, Mar. 3, 1969, abstract 37782c "Formation of 2,6-dioxopiperazine derivatives in the reaction between B-phenylethylamine and ethyl chloracetate" see p. 353.

M. Harfenist et al, J. Org. Chem. vol. 50 1985, "Enantiospecific Synthesis of the trans-9-[3-(3,5-Dimethyl-1-piperazinyl)propyl]carbazoles", pp. 1356-1359.

Primary Examiner—Cecilia Tsang
Attorney, Agent, or Firm—Oblon, Spivak, McClelland, Maier & Neustadt

[57] ABSTRACT

Ergoline derivatives of the formula I:

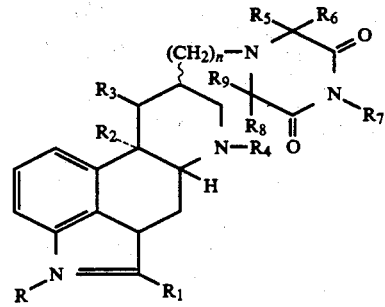

wherein R represents hydrogen or $C_1$–$C_4$ alkyl; $R_1$ represents hydrogen, chlorine, bromine or methyl; either $R_2$ and $R_3$ both represent hydrogen or together represent a chemical bond; $R_4$ represents a $C_1$–$C_4$ hydrocarbon group; each of $R_5$, $R_6$, $R_8$ and $R_9$ independently represents hydrogen or $C_1$–$C_4$ alkyl; $R_7$ represents hydrogen, $C_1$–$C_4$ alkyl, phenyl or $C_3$–$C_7$ cycloalkyl and n is 0, 1 or 2; are prepared by reaction between compounds of the formulae II and III:

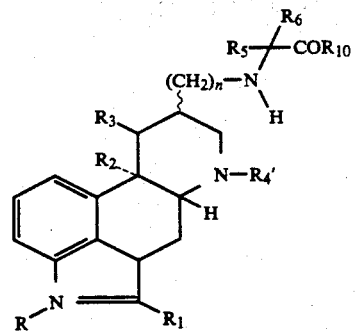

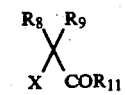

and subsequent cyclization of the resultant compounds. The compounds of the formula I are known useful anxiolytic, antipsychotic and anti-parkinson agents.

6 Claims, No Drawings

PROCESS FOR PREPARING ERGOLINE DERIVATIVES

The present invention provides a process for the preparation of known ergoline derivatives having the formula I:

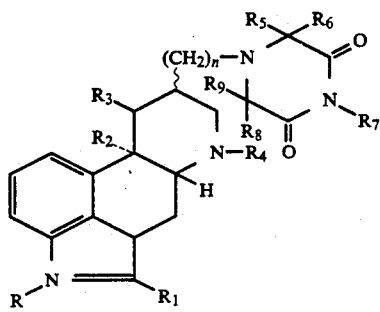

wherein R represents a hydrogen atom or a $C_1$-$C_3$ alkyl group; $R_1$ represents a hydrogen, chlorine or bromine atom or a methyl group; either $R_2$ and $R_3$ represent hydrogen atoms or $R_2$ and $R_3$ together represent a chemical bond; $R_4$ represents a hydrocarbon group having from 1 to 4 carbon atoms; each of $R_5$, $R_6$, $R_8$ and $R_9$ independently represents a hydrogen atom or an alkyl group having from 1 to 4 carbon atoms; $R_7$ represents a hydrogen atom, an alkyl group having from 1 to 4 carbon atoms, a phenyl group or a cycloalkyl group having from 3 to 7 carbon atoms and n is 0, 1 or 2.

In the definition of $R_4$, a hydrocarbon group having from 1 to 4 carbon atoms is intended to include alkyl, cycloalkyl and unsaturated (both ethylenically and acetylenically) groups.

Representative moieties include methyl, ethyl, n-propyl, isopropyl, butyl, t-butyl, isobutyl, methylcyclopropyl, allyl and propargyl.

The invention provides a process comprising (i) reacting an ergoline of the formula II with α-halogen derivatives of formula III to afford ergoline derivatives of formula IV

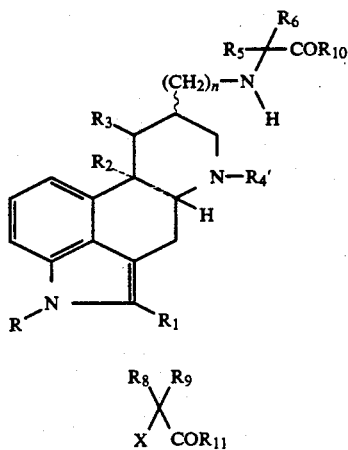

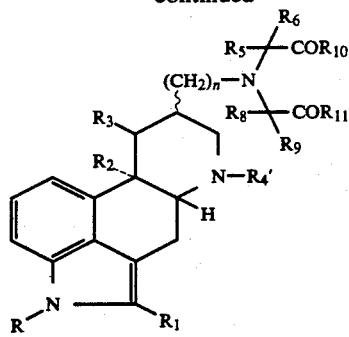

wherein n, R, $R_1$, $R_2$, $R_3$, $R_5$, $R_6$, $R_8$ and $R_9$ have the above given meanings, $R_{10}$ and $R_{11}$ are independently $C_1$-$C_4$ alkoxy group such as ethoxy or methoxy group or an amino group NH-$R_7$ wherein $R_7$ is as above defined, X is halogen atom such as chlorine or bromine; and $R'_4$ represents a hydrocarbon group having from 1 to 4 carbon atoms or a N-protecting group such as acetyl, tert-butyloxycarbonyl or trichloroethyloxycarbonyl group;

(ii) if $R'_4$ is a N-protecting group in the resultant compound of the formula IV, converting the said compound by deprotection and alkylation into a corresponding compound of the formula IV in which $R'_4$ is $C_1$-$C_4$ hydrocarbon group;

(iii) if $R_{10}$ and $R_{11}$ both represent alkoxy groups in the resultant compound of formula IV, converting the said compound by ammonolysis into a corresponding compound of formula IV in which $R_{10}$ and $R_{11}$ are both amino groups; and (iv) cyclising a said compound of formula IV in which at least one of $R_{10}$ and $R_{11}$ represents an amino group NH$R_7$ wherein $R_7$ is as defined above.

The wavy line ⁓⁓⁓ in formulae I, II and IV indicates that the substituent in the 8-position may be in the α-configuration, i.e. below the plane of the ring, in the β-configuration, i.e. above the plane of the ring, or in both, i.e. a mixture of derivatives of formula I, II or IV is present with some having the substituent in the 8-position in the α-configuration and the rest having the substituent in the 8-position in the β-configuration (a diastereoisomeric mixture).

The condensation process (i) is carried out in an organic solvent such as toluene, acetonitrile, or dimethylformamide in presence of an acid scavenger such as an inorganic carbonate or triethylamine. When the reaction is complete the solvent is removed and the residue is purified by crystallization or chromatography according to well known techniques.

If necessary, a compound of formula IV in which $R'_4$ is a N-protecting group may be converted into another compound of the formula IV in which $R'_4$ is a $C_1$-$C_4$ hydrocarbon group by deprotection with a base, formic acid or Zn/dust followed by alkylation with an appropriate halide derivative ($R_4$-Hal) in the presence of an acid scavenger.

The compounds of formula IV in which $R'_4$ is a N-protecting group are preferred starting compounds when n is 1 and the substituent in the 8-position is in the α-configuration.

If necessary, a compound of formula IV in which $R_{10}$ and $R_{11}$ are both alkoxy groups may be converted into another compound of the formula IV in which $R_{10}$ and $R_{11}$ are both amino groups by ammonolysis in a suitable solvent such as methanol, ethanol or dimethylformamide.

According to the present invention, the intermediate derivatives of formula IV are then cyclized to give the derivatives of formula I. In particular, when $R_{10}$ and $R_{11}$ are both amino groups the cyclization to give an ergoline derivative of the formula I where $R_7$ is a hydrogen atom can be accomplished by heating in suitable solvents such as phenol, xylenol or cresol in the range of temperature varying from 100° to 200° C.

When $R_{10}$ is an alkyloxy group and $R_{11}$ is an amino group NH-$R_7$ the cyclization to give an ergoline derivative of the formula I can be carried out by heating in vacuo at the melting point of the compound of formula IV or by the hydrolysis of the COR$_{10}$ group and subsequent treatment with a suitable condensing agent such as acetic anhydride, alkylchlorocarbonate or diimidazolcarbonyl in a solvent such as tetrahydrofuran, 1,4-dioxane or dimethylformamide within the range of temperature of from 50°-150° C.

The starting compounds of formulae II and III which are employed in the process according to the invention are known compounds or may be prepared by established procedures starting from known compounds. For example, the compounds of the formula II and their preparation are described in our EP-A-0126968.

The compounds of formula I and their pharmaceutically acceptable salts are useful anxiolytic, antipsychotic and anti Parkinson agents, as described in EP-A-197,241, U.S. Pat. No. 4,847,253 and WO 90/04396. The ergoline derivatives of formula I prepared by the present process may therefore be formulated also as a pharmaceutical composition. The composition also comprises a pharmaceutically acceptable carrier or diluent.

The preparation of compounds of general formula I is described in the above cited EP-A-0197,241. Although the process there described is capable of producing derivatives of the general formula I, the process here described is more versatile allowing the synthesis of a higher number of derivatives of general formula I especially when $R_2$ and $R_3$ together represent a chemical bond.

The following Examples illustrate the invention.

EXAMPLE 1

1-Phenyl-4-(6-methyl-9,10-ergolen-8β-yl)-methylpiperazin-2, 6-dione

A solution of 5.08 g (0.015 m) of N-[(6-methyl-9,10-ergolen-8β-yl)methyl]-glycine ethyl ester and 1.03 g (0.0075 m) of potassium carbonate and 3.85 g (0.018 m) of N-phenylbromoacetamide in 200 ml of dimethylformamide was stirred at 50° C. for 4 hours.

The resulting solution was poured into brine and the precipitate was extracted with ethyl acetate. Removal of the solvent and crystallization from ethanol afforded 6.5 g of N-phenylcarbamoylmethyl-N-[(6-methyl-9,10-ergolen-8β-yl)-methyl]-glycine ethyl ester m.p. 196°-197° C.

A solution of 6.5 g (0.013 m) of this ester in 50 ml of ethanol was tested with 17.9 ml of sodium hydroxide 1M and the resulting solution was heated at 80° C. for 30 minutes. After acidification with 179 ml of hydrochloric acid 1M, the resulting solution was poured into ice water. The precipitate was filtered off and then washed with water, acetone and dried giving 5.1 g of N-phenylcarbamoylmethyl-N-[(6-methyl-9,10-ergolen-8β-yl)methyl]-glycine. m.p. 252°-255° C. To a suspension of 5 (0.011 m) of N-phenylcarbamoylmethyl-N-[( 6-methyl-9,10-ergolen-8β-yl)methyl]-glycine in 50 ml of anhydrous dioxane was added portionwise 1.96 g (0.121 m) of N,N'-diimidazole carbonyl. The resulting solution was refluxed for 3 hours. After removal of the solvent, the residue was poured into chloroform and extracted with a 10% ammonium hydroxide solution. The organic phase was washed with brine and after drying evaporated to dryness. After crystallization from acetone, 4.1 g of the title compounds were obtained m.p. 240°-245° C.

EXAMPLE 2

4-(6-Methyl-9,10-ergolen-8β-yl)methylpiperazin-2,6-dione

Operating as in Example 1, but employing bromoacetamide in place of N-phenylbromoacetamide, N-carbamoylmethyl-N-[(6-methyl-9,10-ergolen-8β-yl)methyl]-glycine ethyl ester was obtained m.p. 172°-74° C. From this N-carbamoylmethyl-N-[(6-methyl-9,10-ergolen-8β-yl)methyl]-glycine was obtained m.p. 242°-243° C. Finally the title compound was obtained in 75% yield m.p. 224°-225° C.

EXAMPLE 3

4-(1,6-Dimethyl-9,10-ergolen-8β-yl)methylpiperazin-2,6-dione

Operating as in Example 2, but employing N-[(1,6-dimethyl-9,10-ergolen-8β-yl)methyl]-glycine ethyl ester in the place of N-[(6-methyl-9,10-ergolen-8β-yl)methyl]-glycine ethyl ester, N-carbamoylmethyl-N-[(1,6-dimethyl-9,10-ergolen-8β-yl)methyl]-glycine ethyl ester was obtained m.p. 180°-183° C. From this N-carbamoylmethyl-N-[(1,6-dimethyl-9,10-ergolen-8β-yl)methyl]-glycine was obtained. m.p. and finally the title compound was obtained in 55% yield m.p. 216°-218° C.

EXAMPLE 4

4-(2-Bromo-6-methyl-9,10-ergolen-8β-yl)methylpiperazin-2,6-dione

Operating as in Example 1, but employing ethyl bromoacetate in place of N-phenylbromoacetamide, and N-[(2-bromo-6-methyl-9,10-ergolen-8β-yl)methyl]-glycine ethyl ester in place of N-[(6-methyl-9,10-ergolen-8β-yl)methyl]-glycine ethyl ester, N-ethoxycarbonylmethyl-N-[(2-bromo-6-methyl-9,10-ergolen-8β-yl)methyl]-glycine ethyl ester was obtained m.p. 93°-96° C.

A solution of 10 g of this ester in 100 ml of methanol saturated with gaseous ammonia was aged at room temperature for 24 hours. Concentration mixture afforded N-carbamoyl methyl-N-[(2-bromo-6-methyl-9,10-ergolen-8β-yl)methyl]-glycine amide in 85% yield m.p. 218°-221° C.

A mixture of 5 g of N-carbamoylmethyl-N-[(2-bromo-6-methyl-9,10-ergolen-8β-yl)methyl]glycinamide and 30 g of phenol was heated under nitrogen at 160° C. for 30 minutes. After cooling, the reaction mixture was taken up in diethyl ether and the precipitate was crystallized twice from acetone affording 3.9 g of the title compound m p. 242°-245° C.

What is claimed is:

1. A process for preparing an ergoline derivative of the formula I:

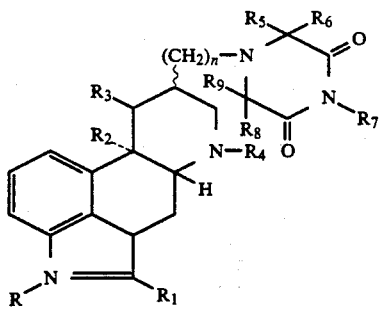

wherein R represents a hydrogen atom or a $C_1$–$C_3$ alkyl group; $R_1$ represents a hydrogen atom, chlorine, bromine atom or a methyl group; either $R_2$ and $R_3$ represent hydrogen atoms or $R_2$ and $R_3$ together represent a chemical bond; $R_4$ represents a hydrocarbon group having from 1 to 4 carbon atoms selected from the group consisting of alkyl, cycloalkyl, ethylenically unsaturated and acetylenically unsaturated groups; each of $R_5$, $R_6$, $R_8$ and $R_9$ independently represents a hydrogen atom or an alkyl group having from 1 to 4 carbon atoms, a phenyl group or a cycloalkyl group having from 3 to 7 carbon atoms and n is 0, 1 or 2, which process comprises reacting an ergoline of the formula II with an α-halogen derivative of the formula III:

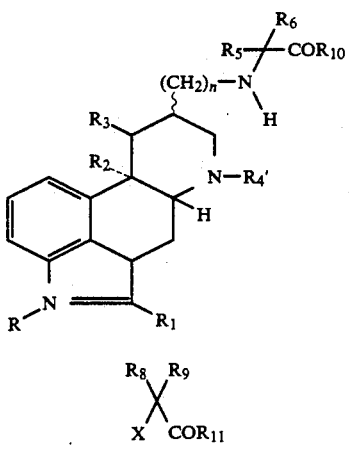

wherein n, R, $R_1$, $R_2$, $R_3$, $R_5$, $R_6$, $R_8$ and $R_9$ have the above given meanings, $R_{10}$ and $R_{11}$ independently represent a $C_1$–$C_4$ alkoxy group or an amino group $NHR_7$ wherein $R_7$ is as defined above, X represents a halogen atom, $R'_4$ represents a hydrocarbon group having from 1 to 4 carbon atoms selected having from 1 to 4 carbon atoms selected from the group consisting of alkyl, cycloalkyl, ethylenically unsaturated and acetylenically unsaturated groups or a N-protecting group and, if necessary, converting the resultant compound of the formula IV:

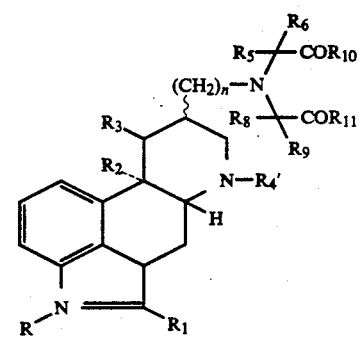

wherein R, $R_1$, $R_2$, $R_3$, $R_5$, $R_6$, $R_8$, $R_9$ and n are as defined above, $R_{10}$ and $R_{11}$ independently represent a $C_1$–$C_4$ alkoxy group or an amino group $NHR_7$ wherein $R_7$ is as defined above and $R'_4$ is a N-protecting group into a compound of the formula IV in which $R'_4$ is a $C_1$–$C_4$ hydrocarbon group selected from the group consisting of alkyl, cycloalkyl, ethylenically unsaturated and acetylenically unsaturated groups by deprotection and alkylation, if necessary converting the compound of the formula IV in which $R_{10}$ and $R_{11}$ both represent an alkoxy group into a compound of the formula IV in which $R_{10}$ and $R_{11}$ are both amino groups by ammonolysis; and cyclizing a said compound of the formula IV in which at least one of $R_{10}$ and $R_{11}$ represents an amino group $NHR_7$ is as defined above.

2. A process according to claim 1 in which the reaction between the compounds of the formulae II and III is carried out in an organic solvent selected from the group consisting of toluene, acetonitrile and dimethylformamide and in the presence of an acid scavenger which is an inorganic carbonate or triethylamine.

3. A process according to claim 1 in which the cyclization of the compound of the formula IV wherein $R_{10}$ and $R_{11}$ both represent amino groups is carried out by heating in a solvent at a temperature of from 100° to 200° C.

4. A process according to claim 3 in which the solvent is phenol, xylenol or cresol.

5. A process according to claim 1 in which the cyclization of the compound of the formula IV wherein $R_{10}$ is an alkoxy group and $R_{11}$ represents a said group $NHR_7$ is carried out by heating in vacuo at the melting point of the compound of formula IV or by hydrolysis of the $COR_{10}$ carboxylate group and subsequent treatment with a condensing agent in a solvent at a temperature of from 50° to 150° C.

6. A process according to claim 5 in which the condensing agent is acetic anhydride, alkylchlorocarbonate or diimidazolcarbonyl and the solvent is tetrahydrofuran, 1,4-dioxane or dimethylformamide.

* * * * *